(12) United States Patent
Lu

(10) Patent No.: US 11,815,503 B2
(45) Date of Patent: Nov. 14, 2023

(54) DETERMINING SOURCE ROCK MATURITY BASED ON HYDROGEN ISOTOPES

(71) Applicant: Saudi Arabian Oil Company, Dhahran (SA)

(72) Inventor: Feng Hu Lu, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 93 days.

(21) Appl. No.: 17/520,980

(22) Filed: Nov. 8, 2021

(65) Prior Publication Data

US 2023/0145385 A1 May 11, 2023

(51) Int. Cl.
*G01N 33/24* (2006.01)

(52) U.S. Cl.
CPC ......... *G01N 33/246* (2013.01); *G01N 33/241* (2013.01)

(58) Field of Classification Search
CPC .......................... G01N 33/241; G01N 33/246
See application file for complete search history.

(56) References Cited

U.S. PATENT DOCUMENTS

| | | |
|---|---|---|
| 2,874,565 A | 2/1959 | Kelton |
| 5,241,859 A | 9/1993 | Smith |
| 5,359,194 A | 10/1994 | Moss |
| 5,388,456 A | 2/1995 | Kettel et al. |
| 6,898,912 B2 | 5/2005 | Bravinski |
| 10,823,716 B2 | 11/2020 | Lu |
| 11,066,929 B2 | 7/2021 | Lu |
| 11,313,224 B2* | 4/2022 | Hakami ............... E21B 49/02 |
| 2017/0226851 A1* | 8/2017 | Hakami ............... E21B 47/07 |

(Continued)

OTHER PUBLICATIONS

Nederlof et al. "Understanding Fluid Variations in the Arab Formation in Abu Dhabi: New Technlogies for Detailed Reservoir Fluid Characterisation" Society of Petroleum Engineers SPE-211618-MS (Year: 2022).*

(Continued)

*Primary Examiner* — John Fitzgerald
(74) *Attorney, Agent, or Firm* — Fish & Richardson P.C.

(57) ABSTRACT

A computer receives a measured wetness of and a measured $\delta^2H$ value associated with a test gas sample from a hydrocarbon formation. The measured wetness is a molar ratio of heavy gas compounds over a total gas within the measured sample. The computer receives calculated wetnesses calculated $\delta^2H$ values associated with a gas samples taken from one or more analogous hydrocarbon reservoirs. The measured wetness received for the test gas sample is identified from among the plurality of calculated wetnesses. The computer determines a corresponding $\delta^2H$ value from among the calculated $\delta^2H$ values that corresponds to the measured wetness of the test gas sample. The computer determines a predicted sample $VR_o$ (vitrinite reflectance equivalent) for the test gas sample based on the corresponding $\delta^2H$ value and a correlation of $\delta^2H$ values to $VR_o$ values. Hydrocarbons are produced from the hydrocarbon formation based on the predicted sample $VR_o$.

7 Claims, 4 Drawing Sheets

(56) References Cited

U.S. PATENT DOCUMENTS

| | | |
|---|---|---|
| 2019/0055842 A1 | 2/2019 | Lu |
| 2019/0212314 A1* | 7/2019 | Lu .................... G01N 33/225 |
| 2023/0138017 A1* | 5/2023 | Lu .................... G06F 30/20 |
| | | 703/10 |

OTHER PUBLICATIONS

Berner and Faber, "Maturity related mixing model for methane, ethane and propane, based on carbon isotopes," Org. Geochem. vol. 13, Sep. 25, 1988, 6 pages.

Burruss et al., "Carbon and hydrogen isotopic reversals in deep basin gas: evidence for limits to the stability of hydrocarbons," Org. geochem., 2010, 41: 1285-1296, 12 pages.

Chi et al., Diagenetic history and porosity evaluation of Upper Carboniferous sandstones from the Spring Valley #1 well, Maritimes Basin, Canada-implications for reservoir development, Journal of Geochemical Exploration, vol. 80, No. 2-3, Sep. 1, 2003, 21 pages.

Chung and Sacket, "Use of Stable Carbon Isotope Compositions of Pyrolytically Derived Methane as Maturity Indices for Carbonaceous Materials," Geochimica et Cosmochimica Acta, vol. 43, Dec. 1979, 10 pages.

Dai et al., "Geochemical characteristics of marine and terrestrial shale gas in China," Marine and Petroleum Geology 76 (2016) 444e463, 20 pages.

Dai et al., "Geochemistry of the extremely high thermal maturity Longmaxi shale gas," Sichuan Basin. Org. Geoch., 2014, 74: 3-12, 10 pages.

Dai et al., "Stable carbon and hydrogen isotopes of gases from the large tight gas fields in China," Science China, Earth Sciences, Jan. 2014, 57:1 (88-103), 16 pages.

De Wit et al., "Multiple Organic Carbon Isotope Reversals across the Permo-Triassic Boundary of Terrestrial Gondwana Sequences: Clues to Extinction Patterns and Delayed Ecosystem Recovery," The Journal of Geology 110, No. 2, Mar. 2002, 21 pages.

Dolan, M.P. et al. "Calibrating Stable Carbon Isotopes of Reservoir Fluids as a Thermal Maturity Indicator," AAPG Search and Discovery Article #90092 © 2009 AAPG Rocky Mountain Section, Jul. 9-11, 2008, Denver, Colorado; Abstract only, 1 page.

Faber, "Zur Isotopengeochemie gasförmiger Kohlenwasserstoffe," Geochemie, Erdöl Erdgas Kohle 103, May 1987, 9 pages.

Galimov, "Isotope organic geochemistry," Organic Geochemistry, 37(10), pp. 1200-1262, Apr. 2006, 63 pages.

Goddard et al., "Novel Gas Isotope Interpretation Tools to Optimize Gas Shale Production Contract: 08122-15," retrieved from URL http://citeseerx.ist.psu.edu/viewdoc/download?doi=10.1.1.397.4161 &rep=rep1&type=pdf, retrieved on Apr. 11, 2019, available on or before Jun. 5, 2013, 90 pages.

Golding et al. "Stable isotope geochemistry of coal bed and shale gas and related production waters: A review," International Journal of Coal Geology 120 (2013) 24-40, 17 pages.

Gurgey et al., "Geochemical and isotopic approach to maturity/ source/mixing estimations for nature gas and associated condensates in the Thrace Basin, NW, Turkey," Applied Geochemistry, Pergamon, Amsterdam, vol. 20, No. 11, Nov. 2005, 21 pages.

Hajikazemi et al., "Chemostratigraphy of Cenomania-Turonian Carbonates of the Sarvak Formation, Southern Iran," Journal of Petroleum Geology, Apr. 1, 2012, 17 pages.

Hitzman et al., "Routine staining of drill core to determine carbonate mineralogy and distinguished carbonate alteration textures," Mineralium Deposita, Nov. 1, 1999, 5 pages.

Huang et al., "Natural gas genesis and sources in the Zizhou gas field, Ordos Basin, China," Research Institute of Petroleum Exploration & Development, 2015, 13 pages.

Jarvis et al., "Secular variation in Late Cretaceous carbon isotopes: a new 13C carbonate reference curve for the Cenomanian-Campanian (99.6—70.6 Ma)," Kingston University London, Geological Magazine, vol. 143, No. 5, Sep. 2006, 49 pages.

Laughrey et al, "Limits to Hydrocarbon Stability in Deep Basins: Evidence from Stable Isotope Reversals and Noble Gas Geochemistry," EAGE Shale Workshop Conference, Nice, Paris, Apr. 2010, 2 pages.

Lillis, P.G. et al. "Petroleum systems of the San Joaquin Basin Province—geochemical characteristics of gas types: Chapter 10 in Petroleum systems and geologic assessment of oil and gas in the San Joaquin Basin Province, California." U.S. Geological Survey, 2008, 30 pages.

Ni et al., "Fundamental studies on kinetic isotope effect (KIE) of hydrogen isotope fractionation in natural gas systems," Geochimica et Cosmochimica Acta, 2011, 75, 2696-2707, 12 pages.

Norville et al., "Carbon and hydrogen isotopic variations of natural gases in the Southeast Columbus basin offshore southeastern Trinidad, West Indies—clues to origin and maturity," Applied Geochemistry, Pergamon, Amsterdam, vol. 22, No. 9, Aug. 24, 2007, 9 pages.

Peters et al., "Carbon and hydrogen stable isotope variations in kerogen during laboratory-simulated thermal maturation," Am. Assoc. Petrol. Geol. Bull., 1981, 65(3), 501-508, 8 pages.

Retallack and Jahren, "Methane Release from Igneous Intrusion of Coal during Late Permian Extinction Events," University of Oregon, Eugene Oregon, the Journal of Geology, vol. 116, Issue 1, Jan. 2008, 21 pages.

Schmid et al., "Carbon isotope stratigraphy using carbonate cements in the Triassic Sherwood Sandstone Group: Corrib Field, west of Ireland," Chemical Geology, Elsevier Science Publisher B.V. Amsterdam, vol. 225, No. 1-2, 2006, 19 pages.

Tang et al., "A kinetic model for thermally induced hydrogen and carbon isotope fractionation of individual n-alkanes in crude oil," Geochim. Cosmochim. Acta, 2005, 69(18), 4505-4520, 16 pages.

Tavakoli et al., "Diagenetic controlled reservoir quality of South Pars gas field, and integrated approach," Comptes Rendus—Geoscience, Elsevier, Paris, France, vol. 343, No. 1, Oct. 5, 2010, 17 pages.

Tilley et al., "Gas isotope reversals in fractured gas reservoirs of the western Canadian Foothills: Mature shale gases in disguise," AAPG Bulletin, 2011, 95, 1399-1422, 24 pages.

Wang et al., "Geochemical characteristics and origin of nature gas in southern Jingbian gas field, Ordos Basin, China," Journal of Natural Gas Science and Engineering, Elsevier, Amsterdam, NL, vol. 46, Sep. 9, 2017, 11 pages.

Wang et al., "Raman Geothermometry of Carbonaceous Material in the Basal Ediacaran Doushantuo Cap Dolostone: The Thermal History of Extremely Negative δ13C Signatures in the Aftermath of the Terminal Cryogenian Snowball Earth Glaciation," Precambrian Research, 298: 174-186, 2017, 13 pages.

Whiticar, "Correlation of natural gases with their sources," AAPG Memoir, vol. 60, Jan. 1994, 23 pages.

Xinyu et al., "Isotopic reversals with respect to maturity trends due to mixing of primary and secondary products in source rocks," Chemical Geology, Elsevier Science Publisher, vol. 339, Aug. 4, 2012, 8 pages.

Zou, Caineng, "The Characteristics and Significance of Conventional and Unconventional Sinian-Lilurian Gas Systems in the Sichuan Basin, central China", Mar. 2015; 17 pages.

Zumberge et al., "Isotopic reversal ('rollover') in shale gases produced from the Mississippian and Fayetteville formations," Marine and petroleum geology, 2012, 31: 43-52, 10 pages.

\* cited by examiner

DETERMINING SOURCE ROCK MATURITY BASED ON HYDROGEN ISOTOPES

TECHNICAL FIELD

This disclosure relates to determining maturity of source rocks in geologic formations.

BACKGROUND

Hydrogen isotopes of natural gas can be utilized to calculate maturity of gas and source rocks found within a geologic formation. The maturity of either the gas or the source rock can be an indication of the suitability of the geologic formation for hydrocarbon production. As kerogen is progressively cracking, kinetic effects on isotopic fractionation result in two normal trends in light gaseous compounds from conventional gas fields. For example, the isotope ratio of Hydrogen 2 to Hydrogen 1 increases relative to a standard (this ratio is expressed as $\delta^2H$) as maturity increases.

SUMMARY

This disclosure describes technologies relating to determining source rock maturity based on hydrogen isotopes.

An example of the subject matter described within this disclosure is a method with the following features. A computer receives a measured wetness of and a measured $\delta^2H$ value associated with a test gas sample from a hydrocarbon formation. The measured wetness is a molar ratio of heavy gas compounds over a total gas within the measured sample. The computer receives calculated wetnesses calculated $\delta^2H$ values associated with a gas samples taken from one or more analogous hydrocarbon reservoirs that are analogous to the hydrocarbon formation. The calculated wetness is a molar ratio of heavy gas compounds over a total gas within each of the plurality of gas samples. The measured wetness received for the test gas sample is identified from among the plurality of calculated wetnesses. The computer determines a corresponding $\delta^2H$ value from among the calculated $\delta^2H$ values that corresponds to the measured wetness of the test gas sample. The computer determines a predicted sample $VR_o$ (vitrinite reflectance equivalent) for the test gas sample based on the corresponding $\delta^2H$ value and a correlation of $\delta^2H$ values to $VR_o$ values. The $VR_o$ values correlate to gas maturity. Hydrocarbons are produced from the hydrocarbon formation by a hydrocarbon production system based on the predicted sample $VR_o$.

Aspects of the example method, which can be combined with the example method alone or in combination with other aspects, include the following. Determining the corresponding $\delta^2H$ value from among the calculated $\delta^2H$ values includes determining an equation to best fit the calculated $\delta^2H$ values and the calculated wetnesses. The equation is used to create a reference line. A plot is generated with the reference line by the computer. The plot has a Y-axis representative of a range of the calculated $\delta^2H$ values and an X-axis representative of a range of calculated wetnesses. The measured wetness is identified on the plot. A $\delta^2H$ value corresponding to the measured wetness is identified from the reference line.

Aspects of the example method, which can be combined with the example method alone or in combination with other aspects, include the following. The equation is:

$$\delta^2H(C_1) = -0.35W - 114.5$$

where $\delta^2H(C_1)$ corresponds to values of $\delta^2H$ of methane in the plurality of gas samples, and "W" corresponds to the plurality of calculated wetnesses of the plurality of gas samples.

Aspects of the example method, which can be combined with the example method alone or in combination with other aspects, include the following. The measured wetness is determined to be within a specified range of values. The specified range of values is indicative of an isotopic reversal.

Aspects of the example method, which can be combined with the example method alone or in combination with other aspects, include the following. The specified range of values for the measured wetness ranges 0% through 7%.

Aspects of the example method, which can be combined with the example method alone or in combination with other aspects, include the following. The measured wetness is determined to be above a specified threshold value. The specified threshold is a threshold indicative of a lack of isotopic reversal.

Aspects of the example method, which can be combined with the example method alone or in combination with other aspects, include the following. The specified value for the measured wetness is above 7%.

Aspects of the example method, which can be combined with the example method alone or in combination with other aspects, include the following. The measured wetness of the test gas sample is determined by a gas chromatograph.

An example of the subject matter described within this disclosure is a method with the following features. A test gas sample is received from a wellbore within a test hydrocarbon formation. A measured wetness of the test gas sample is determined. A measured $\delta^2H$ value associated with the test gas sample is determined. Calculated $\delta^2H$ values are received from a gas samples with a corresponding calculated wetnesses of gas samples. The gas samples are taken from one or more analogous hydrocarbon formations that are analogous to the test hydrocarbon formation. The measured wetness of the test gas sample is identified from the calculated wetnesses. A corresponding $\delta^2H$ value is determined from among the calculated $\delta^2H$ values that corresponds to the measured wetness of the test gas sample. The measured $\delta^2H$ value is adjusted to equal the corresponding $\delta^2H$ value to provide an adjusted $\delta^2H$ value. A predicted sample $VR_o$ (vitrinite reflectance equivalent) is determined for the test gas sample based on the adjusted $\delta^2H$ value and a correlation of $\delta^2H$ values to $VR_o$ values. The $VR_o$ values correlate with a gas maturity. Hydrocarbons are produced from the hydrocarbon formation based on the predicted sample $VR_o$.

Aspects of the example method, which can be combined with the example method alone or in combination with other aspects, include the following. Determining the corresponding $\delta^2H$ value from among the calculated $\delta^2H$ values comprises determining a best-fit equation from the calculated $\delta^2H$ values and the plurality of calculated wetnesses. The best-fit equation is used to create a reference line.

Aspects of the example method, which can be combined with the example method alone or in combination with other aspects, include the following. The best-fit equation is:

$$\delta^2H(C_1) = -0.35W - 114.5$$

where $\delta^2H(C_1)$ corresponds to values of $\delta^{13}C$ of methane in the gas samples and "W" corresponds to the calculated wetnesses of the plurality of gas samples.

Aspects of the example method, which can be combined with the example method alone or in combination with other aspects, include the following. The measured wetness is determined to be below a threshold value. Being at or below the threshold value is indicative of an isotopic reversal.

Aspects of the example method, which can be combined with the example method alone or in combination with other aspects, include the following. The threshold value for the measured wetness is 7%.

Aspects of the example method, which can be combined with the example method alone or in combination with other aspects, include the following. The measured wetness of the test gas sample is determined by a gas chromatograph.

An example of the subject matter described within this disclosure is a method with the following features. A computer system receives a dataset comprising calculated wetnesses of and calculated $\delta^2H$ values associated with hydrocarbon gasses. The computer system determines a reference line from the dataset. The computer plots the reference line on a plot. The computer plots a sample wetness of and a sample $\delta^2H$ value associated with a received gas sample received from a hydrocarbon formation on the plot with the reference line to produce a plotted point. The computer system increases a $\delta^2H$ value of the plotted point to provide an adjusted plotted point so that a $\delta^2H$ value of the adjusted plotted point matches the reference line. The computer system determines an adjusted $\delta^2H$ value from the adjusted plotted point. The adjusted $\delta^2H$ value is the $\delta^2H$ value of the adjusted plotted point. The computer system determines a predicted sample $VR_o$ (vitrinite reflectance equivalent) for the received gas sample based on the adjusted $\delta^2H$ value and a correlation of $\delta^2H$ values to $VR_o$ values. The $VR_o$ values correlate with gas maturity.

Aspects of the example method, which can be combined with the example method alone or in combination with other aspects, include the following. The determined predicted sample $VR_o$ correlates to a maturity level associated with hydrocarbon presence. Hydrocarbons are produced from the hydrocarbon formation based on the correlated gas maturity.

Aspects of the example method, which can be combined with the example method alone or in combination with other aspects, include the following. A difference between the sample wetness and the reference line is determined to exceed a specified threshold.

Aspects of the example method, which can be combined with the example method alone or in combination with other aspects, include the following. The threshold is greater than or equal to a 10% difference.

Aspects of the example method, which can be combined with the example method alone or in combination with other aspects, include the following. The reference line is defined by:

$$\delta^2H(C_1) = -0.35W - 114.5$$

where $\delta^2H(C_1)$ corresponds to values of $\delta^2H$ of methane in the dataset and "W" corresponds to the calculated wetnesses in the dataset.

Aspects of the example method, which can be combined with the example method alone or in combination with other aspects, include the following. The wetness of the received gas sample is determined by a gas chromatograph.

Aspects of the example method, which can be combined with the example method alone or in combination with other aspects, include the following. Wetness is defined by the following equation:

$$W = 100(C2+C3+C4+C5)/(C1+C2+C3+C4+C5)$$

where "W" is a wetness percentage, where "C1" is a molar percentage of methane within a hydrocarbon gas, where "C2" is a molar percentage of ethane within the hydrocarbon gas, where "C3" is a molar percentage of propane within the hydrocarbon gas, where "C4" is a molar percentage of butane within the hydrocarbon gas, and where C5 is a molar percentage of pentane within the hydrocarbon gas.

Particular implementations of the subject matter described in this disclosure can be implemented so as to realize one or more of the following advantages. Correcting $\delta^2H$ values results in more accurate maturity assessments and fewer resulting miss-drilled production wells. In other words sweet spots for either oil, wet gas or dry gas, can be determined based on maturity correctly determined by hydrogen isotopes will help plan operations of exploration and production.

The details of one or more implementations of the subject matter described in this disclosure are set forth in the accompanying drawings and the description below. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

In some instances, hydrogen isotope ratios in light gas compounds from unconventional shale gas do not change linearly. Instead, the linear trend reverses as maturity increases in certain instances. The phenomena can occur in unconventional tight shale, sandstone, and in conventional gas fields. In the context of this disclosure, high maturity can be at least Vitrinite Reflectance Equivalent $(VR_o) = 2.0\%$ for example. In an unconventional reservoir, when $VR_o > 2.0\%$, an isotope reversal can occur. Over mature gas, in the context of this disclosure, $VR_o > 3\%$. However, this range can extend between 2.5% to 3.5% depending on the reservoir. When isotopic reversal occurs, the measured $\delta^2H$ value does not always correspond to a corresponding $VR_o$ within a look-up table. That is, maturity cannot be calculated by using isotopes from $\delta^2H$ values and corresponding look-up tables directly.

This disclosure relates to correcting reversed hydrogen isotopes of gases, and then applying the corrected isotope values to a look-up table to calculate gas maturity using a corrected $\delta^2H$ value. To do so, a relationship between wetness and hydrogen isotopes is established. As maturity increases, wetness of natural gas decreases. As a result, wetness can be used as an indicator for maturity. As wetness decreases, $\delta^2H$ values generally increase based on data from conventional and unconventional gas fields. When in the region of high wetness (for example, wetness>15%) and low maturity, hydrogen isotopes of methane increase linearly as wetness decreases. As wetness continuously decreases, $\delta^2H$ values of methane generally increase, but isotope reversal occurs particularly when wetness is <7%. That is, rather than $\delta^2H$ values increasing, $\delta^2H$ values drop or reverse the increasing trend around the aforementioned wetness.

Because of the reversal, if a $\delta^2H$ value in this range is applied to look-up table, the resulting calculated maturity would be incorrect.

Figure 1:
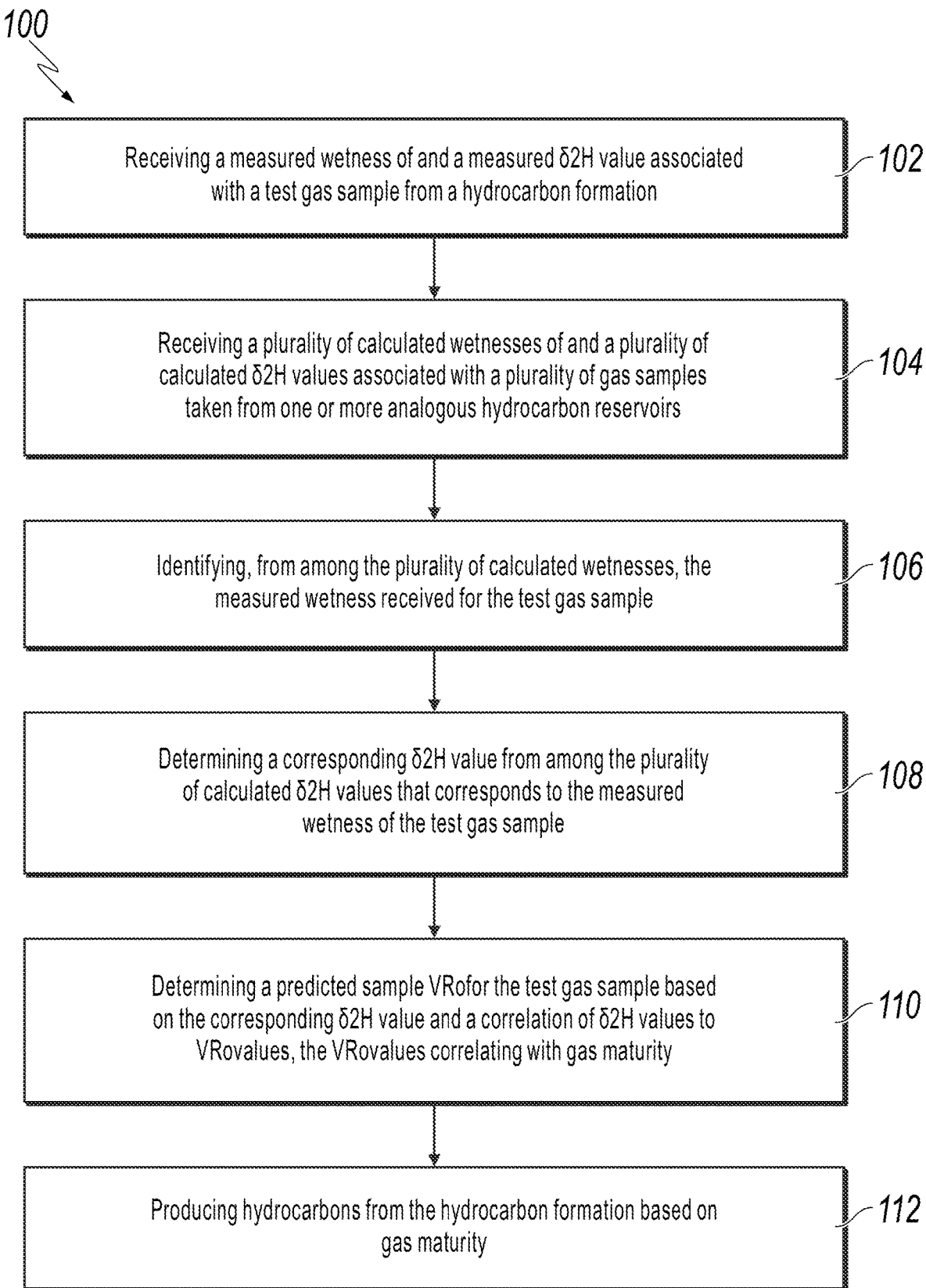
FIG. 1 is a flowchart of a method that can be used with aspects of this disclosure.

FIG. 1 is a flowchart of a method 100 that can be used with aspects of this disclosure. In some implementations, aspects of the method 100 are performed by a computer. At 102, a measured wetness of and a measured $\delta^2H$ value associated with a test gas sample from a hydrocarbon formation, is received. In some implementations, such data are received by a computer. In some implementations, such information is acquired after receiving a test gas sample from a wellbore within a test hydrocarbon formation and determining a measured wetness and a measured $\delta^2H$ value of the test gas sample. The measured wetness is a molar ratio of heavy gas compounds over a total gas within the measured sample. That is, the wetness is defined by equation 1 below:

$$W=100(C2+C3+C4+C5)/(C1+C2+C3+C4+C5) \qquad (1)$$

where "W" is a wetness percentage, where "C1" is a molar percentage of methane within a hydrocarbon gas, where "C2" is a molar percentage of ethane within the hydrocarbon gas, where "C3" is a molar percentage of propane within the hydrocarbon gas, where "C4" is a molar percentage of butane within the hydrocarbon gas, and where "C5" is a molar percentage of pentane within the hydrocarbon gas. In some implementations, the measured wetness of the test gas sample is determined by a gas chromatograph.

$\delta^2H$ is a ratio of Hydrogen 2 isotopes (that is, hydrogen atoms with a proton and a neutron) to Hydrogen 1 isotopes (that is, hydrogen with a single proton and no neutron) compared to a set standard. For example, $\delta^2H$ can be defined by the following equation:

$$\delta^2H(‰)=((^2H/^1H)_{sample}/(^2H/^1H)_{VSMOW})-1)*1000 \qquad (2)$$

where $(^2H/^1H)$ sample is the molar ratio of hydrogen 2 to hydrogen 1 (hydrogen with no neutrons), and where $(^2H/^1H)_{VSMOW}$ is the molar ratio of hydrogen 2 to hydrogen 1 within a standard gas composition. As illustrated and described within this disclosure, the Vienna Standard Mean Ocean Water is used; however, other standards can be used without departing from this disclosure.

At 104, a plurality of calculated wetnesses of and a plurality of calculated $\delta^2H$ values are received. This dataset is associated with a plurality of gas samples taken from one or more analogous hydrocarbon reservoirs that are analogous to the hydrocarbon formation. That is, the analogous hydrocarbon reservoir has characteristics similar to the hydrocarbon formation. In some implementations, the dataset including the calculated wetnesses of and a plurality of calculated $\delta^2H$ values, is received by a computer.

Figure 2:
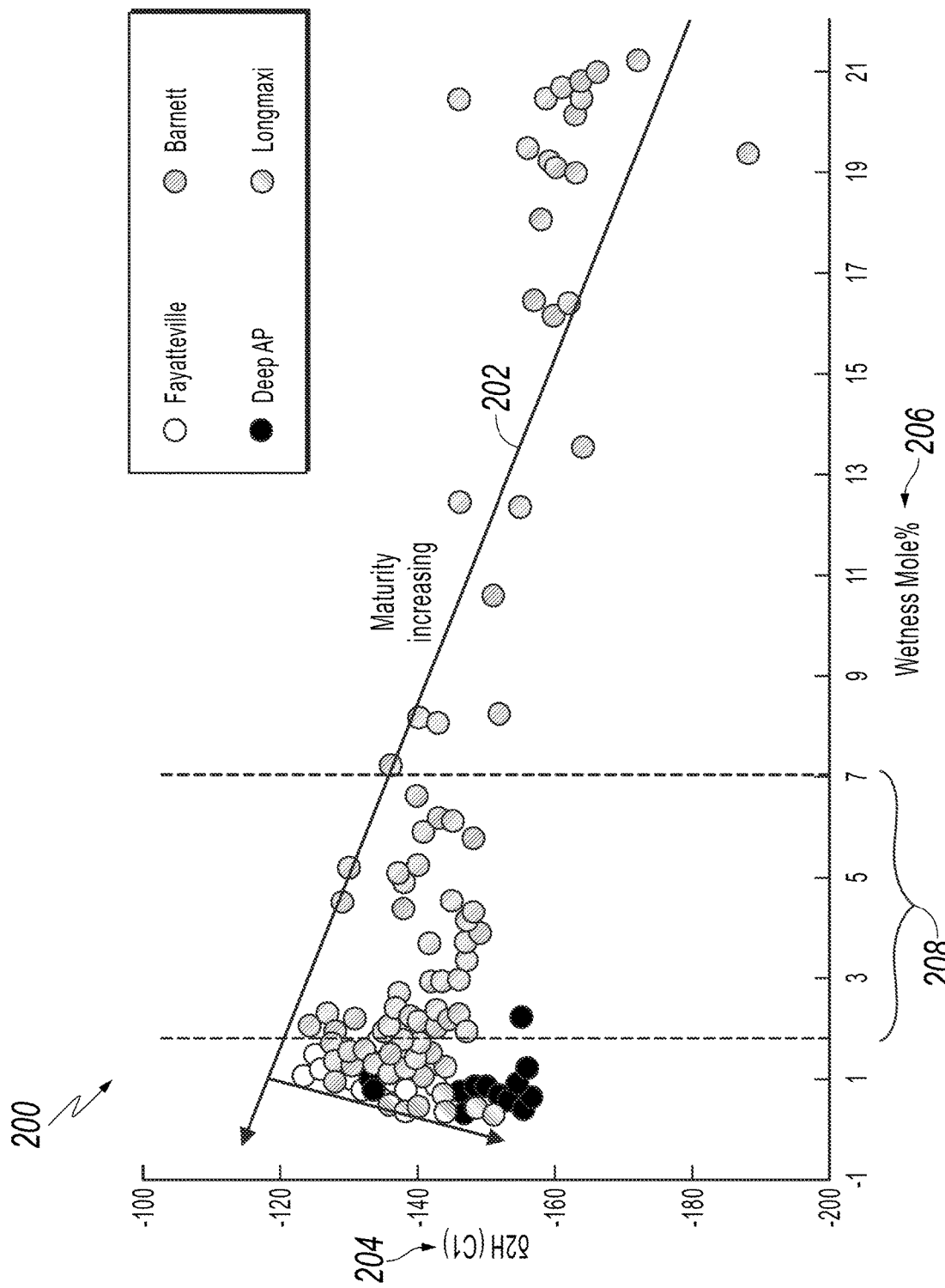
FIG. 2 is a plot of $\delta^2H$ values versus wetness values.

The method described in FIG. 1 is now described with reference to FIG. 2. FIG. 2 is a plot 200 of $\delta^2H$ values versus wetness values. In some implementations, an equation determining to best fit the calculated $\delta^2H$ values and the calculated wetnesses is determined by a computer. This equation, which in some implementations is determined by a computer, is then used to create a reference line 202. The plot 200 is generated with the reference line 202. In some implementations, the plot is generated and produced by the computer 402 (See FIG. 4). The plot has a Y-axis 204, representative of a range of the calculated $\delta^2H$ values, and an X-axis 206 representative of a range of calculated wetnesses.

In some implementations, the equation for the reference (best-fit) line is:

$$\delta^2H(C_1)=-0.35W-114.5 \qquad (3)$$

where $\delta^2H(C_1)$ corresponds to values of $\delta^2H$ of methane in the gas samples, and "W" corresponds to the plurality of calculated wetnesses of the gas samples. In some implementations, such a reference line can be determined by the computer 402.

At 106, the measured wetness of the test gas sample is identified from the calculated wetnesses. There is a range 208 of wetness values in which an isotopic reversal occurs. In some instances, this range is between substantially 0% through 7%. In instances where the measured wetness is over 7%, a sample $VR_o$ (vitrinite reflectance equivalent) for the test gas sample can be determined based on the measured $\delta^2H$, by looking up a corresponding $VR_o$ value within a look-up table. The looked-up $VR_o$ value correlates with gas maturity. $VR_o$ is sometimes expressed as a percentage of light reflected back to a light detector. In general, the greater the percentage of light, the greater the maturity. Different types of hydrocarbons have different maturity windows (that is, ranges of reflected light) in which production is likely to occur. In general, the $VR_o$ is correlated to the maximum burial heating (that is, the greatest temperature experiences by a sample in situ) of a sample. Various types of $VR_o$ measurements can be used without departing from this disclosure. For example, random $VR_o$, maximum $VR_o$, minimum $VR_o$, or any combination can be used.

Figure 3:
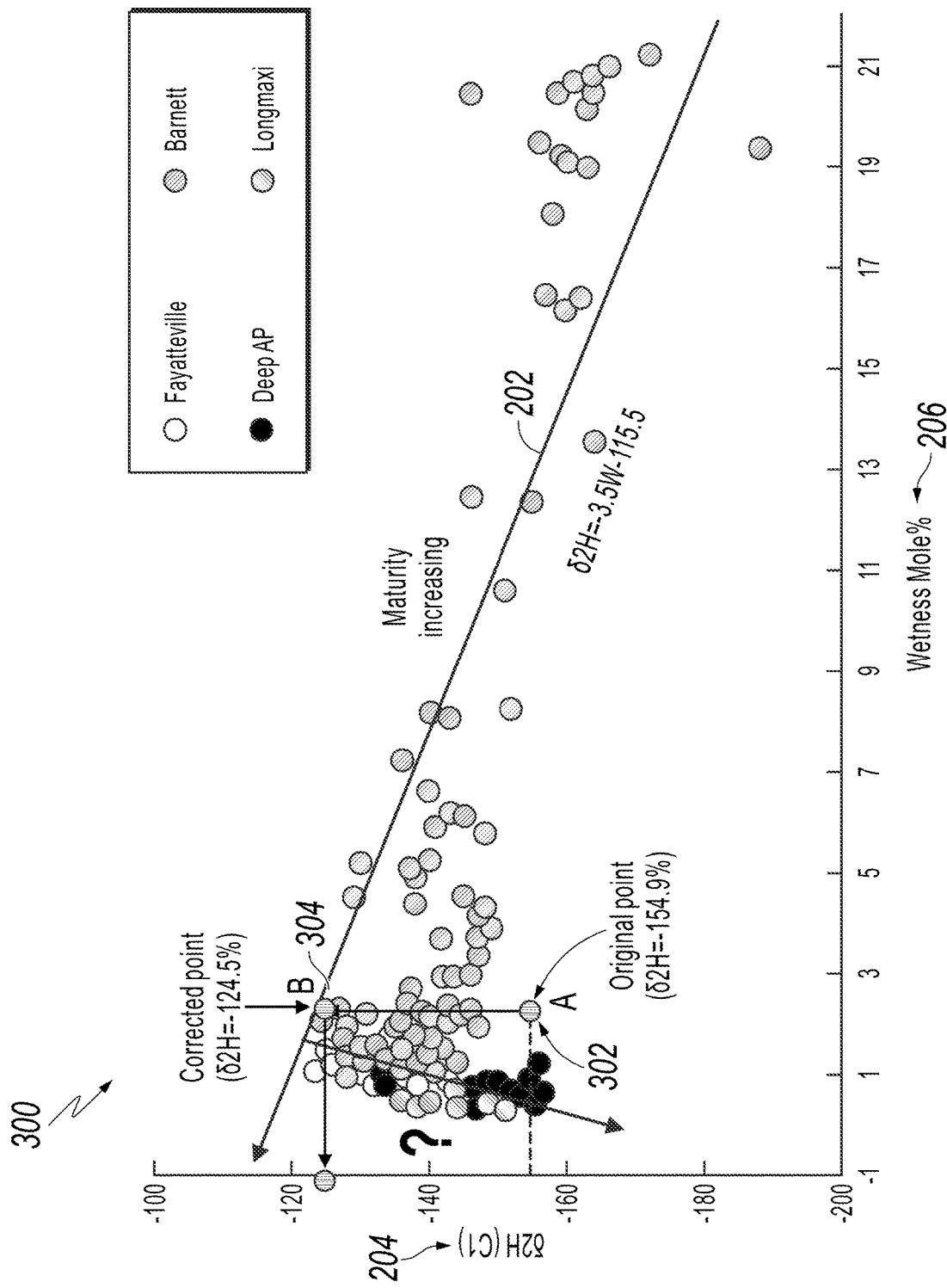
FIG. 3 is an annotated plot of $\delta^2H$ values versus wetness values.

In instances when the range is within the 0-7% range, a range that is indicative of isotropic reversal, then a corrected $\delta^2H$ is determined prior to determine the corresponding $VR_o$. Similarly, such correction can be useful when the measured $\delta^2H$ value exceeds the best fit line, such as EQ. 3, by 10% or more. Such a correction process is illustrated in FIG. 3. FIG. 3 is an annotated plot 300 of $\delta^2H$ values versus wetness values.

For the illustrated example, point "A" 302 is the point corresponding to the wetness value of the sample. That is, point "A" 302 has been identified from among the calculated wetnesses. As the wetness in this example falls within a range indicative of isotropic reversal, a correction is applied to the $\delta^2H$ value.

That is, a $\delta^2H$ value of the plotted point is increased, for example, by a computer, to provide an adjusted plotted point so that a $\delta^2H$ value of the adjusted plotted point "B" 304 that matches the reference line 202. In other words, a $\delta^2H$ value corresponding to the measured wetness is identified from the reference line, and the measured $\delta^2H$ value is adjusted to equal the corresponding $\delta^2H$ value to provide an adjusted $\delta^2H$ value. That is, a corresponding $\delta^2H$ value, from among the calculated $\delta^2H$ values, corresponds to the measured wetness of the test gas sample. Based on the adjusted plotted point "B" 304, the new, adjusted $\delta^2H$ value (point "C" 306) is determined. The adjusted $\delta^2H$ value is then used to determine the $VR_o$ value from within the look-up table.

At 110, a predicted sample $VR_o$ for the test gas sample is determined based on the corresponding $\delta^2H$ value and a correlation of $\delta^2H$ values to $VR_o$ values. As discussed throughout this disclosure, the $VR_o$ values correlate with gas maturity. Such a determination can be made with a look-up table and can be performed, in some instances, by a computer.

Once a maturity is determined based on the corresponding $VR_o$ value, an assessment is made as to whether or not the determined maturity corresponds with a specified hydrocarbon window. Assuming the determined maturity is within the desired window, or range, then, at 112, hydrocarbons are produced, by a hydrocarbon production system, from the hydrocarbon formation based on the predicted sample $VR_o$ (maturity).

Implementations of the subject matter and the operations described in this disclosure can be implemented in digital electronic circuitry, or in computer software, firmware, or hardware, including the structures disclosed in this disclosure and their structural equivalents, or in combinations of one or more of them, for example, using computer 402. Implementations of the subject matter described in this disclosure can be implemented as one or more computer programs, i.e., one or more modules of computer program instructions, encoded on computer storage medium for execution by, or to control the operation of, data processing apparatus. Alternatively or in addition, the program instructions can be encoded on an artificially-generated propagated signal, e.g., a machine-generated electrical, optical, or electromagnetic signal, which is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium can also be, or be included in, one or more separate physical components or media (e.g., multiple CDs, disks, or other storage devices).

The operations described in this disclosure can be implemented as operations performed by a data processing apparatus on data stored on one or more computer-readable storage devices or received from other sources.

The term "data processing apparatus" encompasses all kinds of apparatus, devices, and machines for processing data, including by way of example a programmable processor, a computer, a system on a chip, or multiple ones, or combinations, of the foregoing. The apparatus can include special purpose logic circuitry, e.g., an FPGA (field programmable gate array) or an ASIC (application-specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

The processes and logic flows described in this disclosure can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for performing actions in accordance with instructions and one or more memory devices for storing instructions and data. Generally, a computer will also include, or be operatively coupled to, receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

To provide for interaction with a user, implementations of the subject matter described in this disclosure can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

Implementations of the subject matter described in this disclosure can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the subject matter described in this disclosure, or any combination of one or more such back-end, middleware, or front-end components. The components of the system can be interconnected by any form or medium of digital data communication, e.g., a communication network 432. Examples of communication networks include a local area network ("LAN") and a wide area network ("WAN"), an inter-network (e.g., the Internet), and peer-to-peer networks (e.g., ad hoc peer-to-peer networks).

The computing system can include clients and servers. A client and server are generally remote from each other and typically interact through a communication network. The relationship of client and server arises by virtue of computer programs running on the respective computers and having a client-server relationship to each other. In some implementations, a server transmits data (e.g., an HTML page) to a client device (e.g., for purposes of displaying data to and receiving user input from a user interacting with the client device). Data generated at the client device (e.g., a result of the user interaction) can be received from the client device at the server.

Figure 4:
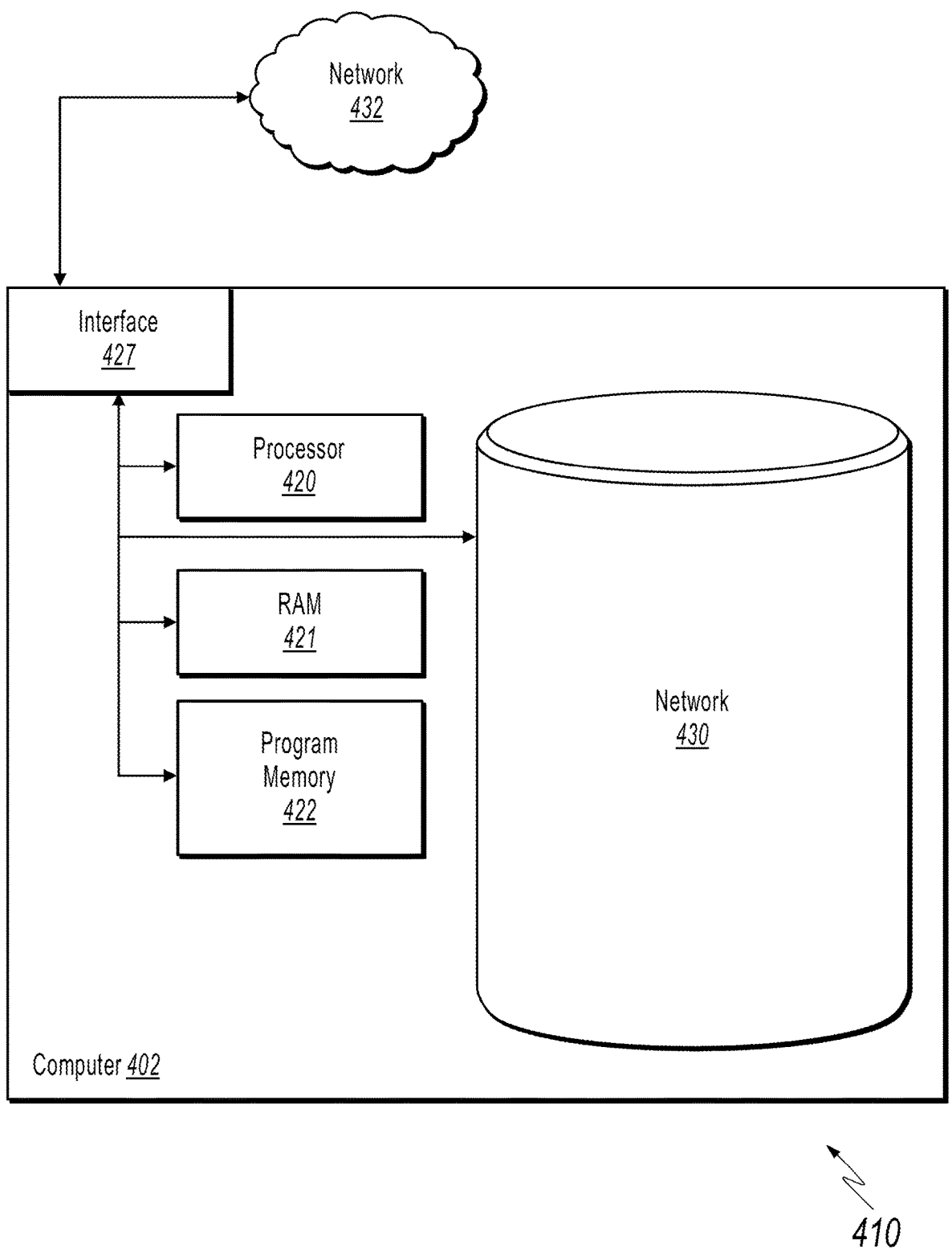
FIG. 4 is a block diagram of an example processing system.

An example of one such type of computer is shown in FIG. 4, which shows a block diagram of a programmable processing system (system) 410 suitable for implementing apparatus or performing methods of various aspects of the subject matter described in this disclosure. The system 410 includes the computer 402 coupled to a network 432. In some instances, a stand-alone, non-networked computer can be used without departing from this disclosure. The computer 402 includes a processor 420, a random-access memory (RAM) 421, a program memory 422 (for example, a writable read-only memory (ROM) such as a flash ROM), and a hard disk 430. The computer 402 can be preprogrammed, in ROM, for example, or it can be programmed (and reprogrammed) by loading a program from another source (for example, from a floppy disk, a CD-ROM, or another computer).

The hard disk 430 is suitable for storing executable computer programs, including programs embodying aspects of the subject matter described in this disclosure, and data including the dataset of wetnesses and $\delta^2 H$ values.

The I/O interface 427 receives and transmits data (e.g., stills, pictures, movies, and animations for importing into a composition) in analog or digital form over communication links such as a serial link, local area network, wireless link, and parallel link.

Also coupled to the I/O interface 427 can be a display, keyboard, or both (not all shown in FIG. 4). Alternatively or in addition, separate connections (separate buses) can be used for the I/O interface 427 and any peripheral components.

While this disclosure contains many specific implementation details, these should not be construed as limitations on the scope of what may be claimed, but rather as descriptions of features specific to particular implementations. Certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. For example, the dataset of wetnesses and $\delta^2 H$ values can be received before, after, or at the same time as receiving the sample wetness and $\delta^2 H$ value. Moreover, the separation of various system components in the implementations described above should not be understood as requiring such separation in all implementations, and it should be understood that the described components and systems can generally be integrated together in a single product or packaged into multiple products.

Thus, particular implementations of the subject matter have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results.

What is claimed is:

1. A method comprising:
receiving, by a computer system, a dataset comprising calculated wetnesses of and calculated $\delta^2 H$ values associated with hydrocarbon gasses;
determining, by the computer system, a reference line from the dataset;
plotting, by the computer system, the reference line on a plot;
plotting, by the computer system, a sample wetness of and a sample $\delta^2 H$ value associated with a received gas sample received from a hydrocarbon formation on the plot with the reference line to produce a plotted point;
increasing, by the computer system, a $\delta^2 H$ value of the plotted point to provide an adjusted plotted point so that a $\delta^2 H$ value of the adjusted plotted point matches the reference line;
determining, by the computer system, an adjusted $\delta^2 H$ value from the adjusted plotted point, wherein the adjusted $\delta^2 H$ value is the $\delta^2 H$ value of the adjusted plotted point; and
determining, by the computer system, a predicted sample $VR_o$ (vitrinite reflectance equivalent) for the received gas sample based on the adjusted $\delta^2 H$ value and a correlation of $\delta^2 H$ values to $VR_o$ values, the $VR_o$ values correlating with gas maturity.

2. The method of claim 1, wherein the determined predicted sample $VR_o$ correlates to a maturity level associated with hydrocarbon presence, the method further comprising producing hydrocarbons from the hydrocarbon formation based on the correlated gas maturity.

3. The method of claim 1, wherein the reference line is defined by:

$$\delta^2 H(C_1) = -0.35W - 114.5$$

where $\delta^2 H (C_1)$ corresponds to values of $\delta^2 H$ of methane in the dataset, and "W" corresponds to the calculated wetnesses in the dataset.

4. The method of claim 1, further comprising determining the wetness of the received gas sample by a gas chromatograph.

5. The method of claim 1, wherein wetness is defined by the following equation:

$$W = 100(C2+C3+C4+C5)/(C1+C2+C3+C4+C5)$$

where "W" is a wetness percentage, where "C1" is a molar percentage of methane within a hydrocarbon gas, where "C2" is a molar percentage of ethane within the hydrocarbon gas, where "C3" is a molar percentage of propane within the hydrocarbon gas, where "C4" is a molar percentage of butane within the hydrocarbon gas, and where C5 is a molar percentage of pentane within the hydrocarbon gas.

6. The method of claim 1, further comprising determining that a difference between the sample wetness and the reference line exceeds a specified threshold.

7. The method of claim 6, wherein the threshold is greater than or equal to a 10% difference.

\* \* \* \* \*